(12) United States Patent
Krishnan et al.

(10) Patent No.: US 6,642,416 B2
(45) Date of Patent: Nov. 4, 2003

(54) PROCESS FOR THE PREPARATION OF 2-[ALKYL(ARYL)]SULFONYLBENZENE-SULFONYL CHLORIDES AND THEIR INTERMEDIATES

(75) Inventors: Lalitha Krishnan, Suffern, NY (US); Bogdan K. Wilk, New City, NY (US); Jennifer P. Varriano, Staten Island, NY (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 10/285,067

(22) Filed: Oct. 31, 2002

(65) Prior Publication Data

US 2003/0109750 A1 Jun. 12, 2003

Related U.S. Application Data

(60) Provisional application No. 60/332,682, filed on Nov. 6, 2001.

(51) Int. Cl.[7] .............................................. C07C 309/78
(52) U.S. Cl. ........................................ 562/828; 568/32
(58) Field of Search ............................ 562/828; 568/28, 568/32

(56) References Cited

U.S. PATENT DOCUMENTS

| | | | |
|---|---|---|---|
| 4,783,285 A | 11/1988 | Josey | |
| 6,531,605 B1 * | 3/2003 | Hogan | .................... 546/294 |

FOREIGN PATENT DOCUMENTS

WO   WO 97/36580   10/1997

OTHER PUBLICATIONS

CA:105:42850 abs of DE 3517821 Mar. 13, 1986.*
CA:131:351078 abs of JP11335348 Dec. 7, 1999.*
G. Pagani, et al., "Studies on cyclic sulfones. –Notes on 4H–1,4–benzothiazines,1–1–dioxide", Gazzetta Chimica Italiana, vol. 97, No. 7, Jul. 1967, pp. 1804–1816.
B. Douglass, et al. "Sulfinate Esters. II. The Sythetic Utility of Methyl Methanesulfinate", Journal of Organic Chemistry vol. 32, No. 2, Feb. 1967, pp. 324–326.
A. McKillop, et al., Sodium Perborate a cheap and effictive reagent for the oxidation of anilines and sulphides, vol. 24, No. 14, 1983, pp. 1505–1508.
A. Courtin, et al.: "Notizen zur Synthese von 2–Aminophenylsulfonen", Helvetica Chimica Acta, vol. 63, No. 6, Sep. 17, 1980, pp. 1412–1419.
H. Meerwein, et al., "Untersuchungen zun Herstellung Diazoverbindungen, II. Verfahren zur Herstellung aromatischer Sulfonsaurechloride, eine Modifikation der Sandmeyer Reaktion", Chemische Berichte, vol. 90, No. 6, 1957, pp. 841–852.

* cited by examiner

*Primary Examiner*—Jean F. Vollano
(74) *Attorney, Agent, or Firm*—Michael R. Nagy

(57) ABSTRACT

A process for the preparation of 2-[alkyl(aryl)] sulfonylbenzene sulfonyl chlorides of the following formula is provided:

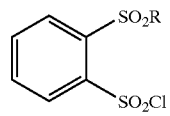

in which R is alkyl or aryl substituted at the ortho or meta positions with alkyl, aryl, NHAc or alkoxy, comprising the steps of:

a) reacting 2-chloronitrobenzene, 2-fluoronitrobenzene or 2-bromonitrobenzene with a compound of the following formula:

$$RSO_2^- M^+$$

wherein R is defined above; and M is sodium, potassium, lithium, ammonium or quaternary ammonium, in a polar aprotic solvent at a temperature of about 50 to 190° C.;

b) reacting the material prepared in step (a) with hydrogen at a pressure of about 20 to about 60 psi in a polar aprotic solvent at a temperature of about 20 to about 60° C.; and c) diazotizing the material prepared in step (b) with sodium nitrite in the presence of hydrochloric acid and reacting the resulting diazonium salt with sulfur dioxide in the presence of copper (I) or copper (II) compounds or a mixture thereof, in water.

8 Claims, No Drawings

PROCESS FOR THE PREPARATION OF 2-[ALKYL(ARYL)]SULFONYLBENZENE-SULFONYL CHLORIDES AND THEIR INTERMEDIATES

This application claims priority from copending provisional application Ser. No. 60/332,682, filed Nov. 6, 2001, the entire disclosure of which is hereby incorporated by reference.

FIELD OF THE INVENTION

This present invention is directed to a novel process for the preparation of 2-[alkyl(aryl)]sulfonylbenzenesulfonyl chlorides and intermediates thereof.

BACKGROUND OF THE INVENTION

2-[alkyl(aryl)]sulfonylbenzenesulfonyl chlorides are compounds known to be useful as intermediates in the production of certain herbicidal compounds as disclosed, e.g., in U.S. Pat. No. 4,783,285. These compounds are also known to be useful as intermediates in the preparation of compounds having activity as protease inhibitors as described, e.g., in PCT Patent Application Publication No. WO 97/36580. In light of the usefulness of these compounds in such production methods, there is a continued need to develop simpler and milder methods for their production.

To date, methods for producing 2-[alkyl(aryl)]sulfonylbenzenesulfonyl chlorides are not entirely acceptable. For example, U.S. Pat. No. 4,783,285 describes a four step process for the synthesis of 2-methylsulfonylbenzene sulfonylchloride which involves the oxidation of an aryl sulfide to an aryl sulfone with sodium periodate and the oxidation of an aryl sulfide to an aryl sulfonyl chloride with chlorine water. However, this method has been found to be disadvantageous since it requires the use of methyl mercaptan and involves the multiple oxidation steps noted above.

Accordingly, the need exists for a simpler, safer method for the production of 2-[alkyl(aryl)]sulfonylbenzenesulfonyl chlorides, which can be used on a large scale.

SUMMARY OF THE INVENTION

The present invention relates to a process for the preparation of 2-[alkyl(aryl)]-sulfonylbenzene sulfonyl chlorides of the formula:

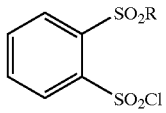

in which R is alkyl or aryl substituted at the ortho or meta positions with alkyl, aryl, NHAc or alkoxy, comprising the steps of:

a) reacting 2-chloronitrobenzene, 2-fluoronitrobenzene or 2-bromonitrobenzene with a compound of the following formula:

wherein R is defined above and M is sodium, potassium, lithium, ammonium or quaternary ammonium, in a polar aprotic solvent at a temperature of about 50 to 190° C.;

b) reacting the material prepared in step (a) with hydrogen at a pressure of about 20 to about 60 psi in a polar aprotic solvent at a temperature of about 20 to about 60° C.; and c) diazotizing the material prepared in step (b) with sodium nitrite in the presence of hydrochloric acid and reacting the resulting diazonium salt with sulfur dioxide in the presence of copper (I) or copper (II) compounds or a mixture thereof, in water.

DETAILED DESCRIPTION OF THE INVENTION

The present invention has utility in producing the desired compounds in higher yields through a shorter, simplified procedure in comparison to prior art processes. The present process further results in a product of higher purity in comparison to known processes, which eliminates the need for further purification. The present process is advantageously readily adaptable to large-scale production.

The present invention is directed to a process for the production of 2-[alkyl-(aryl)]sulfonyl benzenesulfonyl chlorides having the following formula:

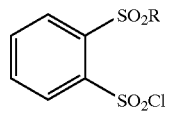

where R is alkyl or aryl substituted at the ortho or meta positions with alkyl, aryl, NHAc or alkoxy, comprising the following steps:

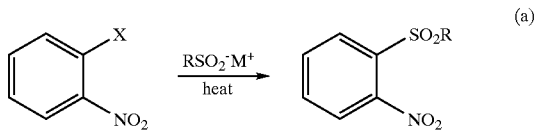

wherein X is chlorine, fluorine, or bromine; M is sodium, potassium, lithium, ammonium or quaternary ammonium; and R is as defined above;

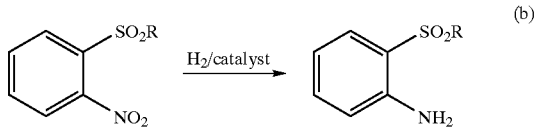

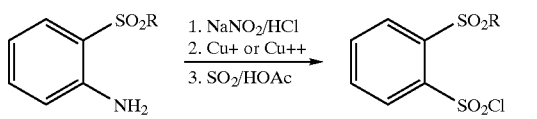

Preferably, R is an alkyl of 1 to 8 carbons or aryl substituted at the ortho or meta positions with alkyl, aryl, NHAc or alkoxy. Most preferably, R is methyl. Preferably, X is bromine.

In reaction step (a), the 2-chloronitrobenzene, 2-fluoronitrobenzene or 2-bromonitrobenzene is reacted with the sulfinate salt of formula $RSO_2^-M^+$ in a polar solvent. The solvent should be aprotic solvent, such as N,N-dimethylformamide, dimethylsulfoxide, N-methyl-2-pyrolidinone, or N,N-dimethylacetamide. Preferably, the solvent is DMSO. The reaction should take place at a temperature of between about 50 to about 190° C., preferably between about 50 to 150° C. and most preferably between about 75 to about 80° C. The reaction should be run until completion, generally within 1 to 24 hours and preferably 1 to 3 hours. The product can be isolated by drowning the reaction mixture in water.

In reaction step (b), the hydrogenation of the nitrophenylsulfone may be run in methanol and dilute sulfuric acid or ethanol to provide aminophenylsulfone as its sulfate salt or as the free base. Preferably, this reaction is run in the presence of 5 to 10 mole percent of a Group VIII metal catalyst, such as Palladium or Rhodium, preferably, Palladium. Reaction step (b) is preferably run in ethanol at a pressure of 35 to 50 psi and a temperature of between about 20 to 40° C. The reaction product from step (b) can be recovered by conventional techniques which will be recognized by one skilled in the art, e.g., filtering off the catalyst and evaporating off the excess solvent from the filtrate to yield the desired product.

Reaction step (c) comprises the diazotization of 2-methylsulfonylaniline with aqueous sodium nitrite in the presence of hydrochloric acid at a temperature of between about −5 to about 10° C., and preferably 0 to about 5° C. This is followed by reaction with sulfur dioxide dissolved in acetic acid. The sulfur dioxide may be gaseous or liquid. Preferably this reaction takes place in the presence of catalytic amounts copper (I) chloride, copper (II) chloride dihydrate or a mixture thereof. The reaction time is generally about 2.5 to 3 hours for complete conversion. The product of reaction step (c) may be isolated via filtration and repeated washing with water to remove traces of the copper salts.

The present invention further encompasses a process for the production of the sulfone intermediate reaction product of reaction step (a). The sulfone intermediate has the following formula:

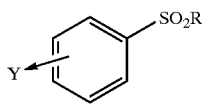

wherein R is alkyl or aryl substituted at the ortho or meta positions with alkyl, aryl, NHAc or alkoxy;

Y is $NO_2$, alkyl sulfate, aryl sulfate, CN, alkyl carbonate, aryl carbonate or CHO when in the 2-position; hydrogen, alkyl, aryl, $NO_2$, alkyl sulfate, aryl sulfate, CN, alkyl carbonate, aryl carbonate, or CHO when in the 3,5 or 6-positions; and hydrogen, alkyl, aryl or $CF_3$ when in the 4-position, which comprises:

reacting 2-chloronitrobenzene, 2-fluoronitrobenzene or 2-bromonitrobenzene derivatives having the Y group as defined above with a compound of the formula:

wherein R is as defined above and M is sodium, potassium, lithium, ammonium, or quaternary ammonium in a polar aprotic solvent at a temperature of about 50–150° C.

As used herein, the terms "alkyl" and "alkoxy" are meant to include both straight and branched chain moieties containing 1–8 carbon atoms. The term "aryl" is meant to include aromatic radicals of 6–12 carbon atoms. The term "halogen" is meant to include fluorine, chlorine, bromine and iodine.

The present invention will now be illustrated by reference to the following specific non-limiting examples.

EXAMPLE 1

2-Methylsulfonyinitrobenzene

Sodium methanesulfinate (33.5 g; 0.29 mol; 1.17 eq) was suspended in DMSO (60 mL). The suspension was gradually heated to 80° C. (it became a clear solution at ca. 70° C). 2-Chloronitrobenzene (39.6 g; 0.25 mol) was dissolved in DMSO (35 mL) and the solution was added dropwise within 20 minutes. The reaction was monitored by HPLC (Prodigy ODS-2, 250×4.6 mm, acetonitrile/water with 0.05% TFA) which, after 3 hours, indicated 2.4% of the starting material was left.

The reaction mixture was allowed to cool to 20° C. and water (250 mL) was added dropwise. The product gradually precipitated out. More water (100 mL) was added and the slurry was stirred for 30 minutes. The solids were filtered, washed with water (3×100 mL), drained thoroughly, and dried at 45° C. in vacuum, overnight to afford 49.9 g (97% yield) of 2-methylsulfonylnitrobenzene. m.p. 102–104.5° C. (lit. 101–103° C.). $^1$H NMR (CDCl$_3$): 8.23–8.21 (m, 1H), 7.88–7.83 (m, 3H), 3.45 (s, 3H). $^{13}$C NMR (DMSO-d$_6$): 149.0, 134.9, 134.0, 132.8, 131.3, 124.9, 45.0. MS (m/e): 201, 186, 139 (100%), 122, 109, 92.

EXAMPLE 2

2-Methylsulfonylaniline

2-Methylsulfonyinitrobenzene (6.0g, 0.03 mol) was suspended in absolute ethanol (60 mL). 6% Pd/C catalyst (50% wet; 1.01 g) was added and the suspension was hydrogenated in a Parr shaker at 40 psi for 16 hours. The catalyst was then filtered over a pad of infusorial earth and washed with ethanol (2×10 ml). The filtrate was concentrated to dryness on a rotary evaporator. 4.94 g (96% yield) of the product was obtained as white crystals. mp 82–84° C. $^1$H NMR (CDCl$_3$) δ 7.7 (dd, 1H), 7.2–7.3 (m, 1H), 6.5–6.8 (m, 2H), 5.04 (bs, 2H), 3.07 (s, 3H); CIMS (m/e) 172 (M+H$^+$, 100%).

EXAMPLE 3

2-Methylsulfonylaniline

2-Methylsulfonylnitrobenzene (13.0 g, 0.065 mol) was suspended in MeOH (140 mL) and 2N H$_2$SO$_4$ (60 mL). 6% Pd/C catalyst (50% wet; 3 g) was added to the suspension and it was hydrogenated at 40 psi in a Parr shaker for 4 hours. The solution was filtered, the catalyst washed twice with 10 mL of MeOH and concentrated on the rotary evaporator to a volume of 80 mL. The suspension was cooled to 5° C. with stirring and 15 mL of aqueous 10 N sodium hydroxide was added and stirred for 30 minutes at 5° C. The solid was filtered, washed with water and dried at 40° C. in vacuum (30 in. Hg) to give 10.5 g (95% yield) of 2-methylsulfonylaniline.

EXAMPLE 4

2-Methylsulfonylbenzenesulfonyl Chloride

2-Methylsulfonylaniline (48 g, 0.28 mole), was added portion-wise with stirring to 365 mL of water, 250 mL of conc. HCl and 60 mL of HOAc. The mixture was cooled to 50° C. and sodium nitrite (22.3 g; 0.32 mole) dissolved in 250 mL water, was added drop-wise with stirring maintaining the temperature between 0–5° C. After complete addition of sodium nitrite, the resulting solution was stirred for 30 minutes at 0–5° C. Sulfur dioxide was bubbled into 200 mL of glacial acetic acid at room temperature for 10 minutes CuCl$_2$·2H$_2$O (11 g; 0.06 mole) and CuCl (3.7 g; 0.037 mole) were added to the HOAc and cooled to 10° C. Sulfur dioxide was bubbled through the suspension for an additional 15 minutes and the diazotized amine was added portionwise with stirring keeping the temperature between 0–5° C.

Sulfur dioxide was bubbled in continuously until the diazotized amine was added completely. After the complete addition of the diazotized amine, bubbling of SO$_2$ was stopped and the green suspension was stirred at 0–5° C. for 3 hours. At the end of 3 hours, the suspension was diluted with water (300 mL), filtered and the solid washed three times with 50 mL of water. The product was dried at room temperature in vacuum (30 in. Hg) to give 46 g of 2-methylsulfonylbenzenesulfonyl chloride (61% yield) as a white solid. mp 135–137° C. (lit. 133–135° C.). $^1$H NMR (CDCl$_3$) δ 8.3–8.6 (m, 2H), 7.87–8.02 (m, 2H), 3.41 (s, 3H). $^{13}$C NMR (CDCl$_3$) δ 142.94, 139.24, 136.61, 135.22, 133.58, 132.13, 45.49. CIMS (m/e) 255 (M+H$^+$, 100%).

EXAMPLE 5

2-Methylsulfonylbenzenesulfonyl Chloride

2-Methylsulfonylaniline (6.0 g; 0.035 mole) was added portionwise, with stirring, to a mixture of 30 mL of water and 30 mL of HCl. The mixture was cooled to 5° C. and sodium nitrite (2.7 g; 0.039 mole) dissolved in water (7 mL) was added dropwise maintaining the temperature between 0–5° C. After complete addition of sodium nitrite, the resulting solution was stirred at 0–5° C. for 30 minutes Sulfur dioxide was bubbled into 18 mL of HOAc for 14 min at room temperature. CuCl (0.8 g; 0.008 mole) was added and cooled to 10° C. Sulfur dioxide was bubbled through the suspension for an additional 15 min and the diazotized amine was added portionwise maintaining the temperature between 0–5° C. After the complete addition of diazotized amine, bubbling of SO$_2$ was stopped and the green suspension was stirred at 0–5° C. for 3 hours. At the end of 3 hours, the suspension was diluted with 50 mL of water, filtered and washed three times with 10 mL of water to give, after drying in vacuum (30 in. Hg), 6.4 g (71% yield) of 2-methylsulfonylbenzenesulfonyl chloride which was characterized by its melting point and spectral data. mp 135–137° C. (lit. 133–135° C.). $^1$H NMR (CDCl$_3$) δ 8.3–8.6 (m, 2H), 7.87–8.02 (m, 2H), 3.41 (s, 3H). $^{13}$C NMR (CDCl$_3$) δ 142.94, 139.24, 136.61, 135.22, 133.58, 132.13, 45.49. CIMS (m/e) 255 (M+H$^+$, 100%).

The present invention may be embodied in other specific forms without departing from the spirit and essential attributes thereof and accordingly, reference should be made to the appended claims, rather than to the foregoing specification, as indicating the scope of the invention.

What is claimed is:

1. A process for the preparation of 2-[alkyl(aryl)] sulfonylbenzene sulfonyl chlorides of the formula:

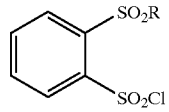

in which R is alkyl or aryl substituted at the ortho or meta positions with alkyl, aryl, NHAc or alkoxy, comprising the steps of:
   a) reacting 2-chloronitrobenzene, 2-fluoronitrobenzene or 2-bromonitrobenzene with a compound of the following formula:

wherein R is defined above; and M is sodium, potassium, lithium, ammonium or quaternary ammonium, in a polar aprotic solvent at a temperature of about 50 to 190° C.;
   b) reacting the material prepared in step (a) with hydrogen at a pressure of about 20 to about 60 psi in a polar aprotic solvent at a temperature of about 20 to about 60° C.; and
   c) diazotizing the material prepared in step (b) with sodium nitrite in the presence of hydrochloric acid and reacting the resulting diazonium salt with sulfur dioxide in the presence of copper (I) or copper (II) compounds or a mixture thereof, in water.

2. A process as in claim 1 wherein the polar solvent in step (a) is selected from the group consisting of N,N-dimethylformamide, dimethylsulfoxide, N-methyl-2-pyrolidinone and N,N-dimethylacetamide.

3. A process as in claim 1, wherein R is alkyl of 1 to 8 carbons.

4. A process as in claim 3, wherein R is methyl.

5. A process as in claim 1 wherein reaction step (a) takes place at a temperature of 50 to 150° C.

6. A process as in claim 1 wherein reaction step (b) takes place at a temperature of 20 to 40° C.

7. A process as in claim 6, wherein reaction step (b) takes place in the presence of 5 to 10 mole percent of a Group VIII metal catalyst.

8. A process as in claim 1, wherein reaction step (c) takes place at a temperature of −5 to 10° C.

* * * * *